(12) United States Patent
Chen et al.

(10) Patent No.: US 7,436,503 B1
(45) Date of Patent: Oct. 14, 2008

(54) DARK FIELD INSPECTION APPARATUS AND METHODS

(75) Inventors: Grace Hsiu-Ling Chen, San Jose, CA (US); Tao-Yi Fu, Fremont, CA (US); Evan Mapoles, San Ramon, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 470 days.

(21) Appl. No.: 11/009,663

(22) Filed: Dec. 10, 2004

Related U.S. Application Data

(60) Provisional application No. 60/598,799, filed on Aug. 3, 2004.

(51) Int. Cl.
  *G01N 21/00* (2006.01)
  *G02B 27/42* (2006.01)
(52) U.S. Cl. .................................. 356/237.1; 250/550
(58) Field of Classification Search ....................... None
  See application file for complete search history.

(56) References Cited

U.S. PATENT DOCUMENTS

| | | | | |
|---|---|---|---|---|
| 5,177,559 A | * | 1/1993 | Batchelder et al. | 356/237.5 |
| 5,355,212 A | * | 10/1994 | Wells et al. | 356/237.4 |
| 5,579,108 A | * | 11/1996 | See | 356/450 |
| 5,617,203 A | * | 4/1997 | Kobayashi et al. | 356/237.5 |
| 6,724,473 B2 | * | 4/2004 | Leong et al. | 356/237.2 |
| 6,774,991 B1 | * | 8/2004 | Danko | 356/237.4 |
| 7,041,998 B2 | * | 5/2006 | Weiss et al. | 356/237.4 |

* cited by examiner

Primary Examiner—Gregory J Toatley, Jr.
Assistant Examiner—Juan D Valentin
(74) Attorney, Agent, or Firm—Weaver Austin Villeneuve & Sampson LLP

(57) ABSTRACT

Accordingly, the present invention provides methods and apparatus for performing a darkfield inspection on a specimen having periodic structures thereon while substantially reducing or eliminating the long range ringing response, which is typically produced by a traditional Fourier filter mask used to eliminate the diffraction caused by the periodic structures. In one embodiment, an apparatus for inspecting a specimen by detecting optical beams scattered from the specimen. The apparatus includes a beam generator for providing and directing an incident beam towards a specimen and an array subtraction device for substantially subtracting a periodic component from an output beam scattered from the specimen in response to the incident beam. The periodic component corresponds to at least one periodic structure on the specimen, and the subtraction is performed so as to substantially reduce or eliminate a ringing response from the output beam. The subtraction is also performed so as to substantially prevent subtracting any actual defect components from the output beam. The apparatus further includes a detector for receiving the output beam and generating an output image or signal based on the output beam.

20 Claims, 6 Drawing Sheets

DARK FIELD INSPECTION APPARATUS AND METHODS

CROSS REFERENCE TO RELATED PATENT APPLICATION

This application claims priority of U.S. Provisional Application No. 60/598,799 filed on Aug. 3, 2004 entitled DARK FIELD INSPECTION APPARATUS AND METHODS, by Chen, et al. which is incorporated herein by reference in its entirety for all purposes.

BACKGROUND OF THE INVENTION

This invention pertains to apparatus and methods for inspecting a specimen, such as a semiconductor wafer or photomask in a dark field inspection system or the like. It also pertains to apparatus and methods for reducing or eliminating from the inspection results the effects contributed by periodic structures on the specimen.

A diverse number and type of inspection systems are available for inspecting samples for defects. One inspection type is referred to as a "darkfield" inspection. Darkfield inspection makes use of light scattered or diffracted by the surface to characterize and examine features of the surface. As used herein, scattered light shall refer to both scattered light and diffracted light.

FIG. 1 is a cross-section view of an illuminated surface used to illustrate aspects of darkfield inspection. An illumination source 101 projects a light beam I (also referred to herein as the incident beam) onto the surface 102 being examined. A portion of the incident beam I is reflected by the surface as the reflected beam R. If the surface 102 areas. In particular, defect detection and analysis are important in semiconductor processing. Defects include, but are not limited to, pits, bumps, scratches, and a number of other features, which mar the surface 102. Thus, the light of an incident beam I is often subject to some degree of scattering. FIG. 1 illustrates a typical incident beam I having a light scattering pattern schematically depicted by a plurality of scattered light rays 103, 104, 105, and 106, which are scattered by a surface defect 108.

Known darkfield inspection tools use detectors to detect the light scattered from the inspection surface. Some designs use as many as three or four distinct and widely separated discrete photodetector elements. Such discrete photodetector element(s) are positioned so that they are not in the path of the reflected beam R. This results in a detection field where the background (the field) is dark. The scattered light received by the detector provides a representation of the surface 102 whereby the surface defects show up as lighter regions against the dark background or field. Hence, the name darkfield scanning.

When a specimen contains periodic structures, such as semiconductor devices on a wafer, these periodic or "array" structures tend to adversely affect the darkfield inspection results. Although these periodic structures are not considered to be defects, these structures result in scattered light during the darkfield inspection. Since the defects also result in scattered light, the scattered light from the actual defect is not easily distinguishable from the scattered light from the periodic non-defect structures. Thus, the periodic structures contribute noise to the scattered light from the specimen, which is analyzed for defects.

One goal is to eliminate or reduce the contribution of noise resulting from periodic structures on a specimen undergoing darkfield inspection. One technique is to place a Fourier filter in the pupil plane to block scattered light produced by the periodic structures. Since the scattering due to the periodic structure results in diffraction peaks in the pupil plane, the Fourier filter, typically implemented as a hard mask, can be designed to physically block these diffraction peaks from reaching the detectors of the inspection system.

In general, there are two kinds of darkfield inspection tools. The first kind illuminates the sample with spot scanning technology and collects the scattering without any imaging optics. The resolution of this kind is determined by the size of the scanning spot. This kind of system is referred herein as a non-imaging darkfield system. The second kind of darkfield inspection tool "floods" the sample with light and collects the scattered energy with a set of imaging optics and imaging detector (such as a CCD or TDI). Unlike the first kind, the resolution of the second kind is determined by the collection numerical aperture (NA). This kind of system is referred herein as an imaging darkfield system.

Although conventional masks for blocking diffraction peaks from periodic structure are effective and leave no adverse side effects for the non-imaging darkfield system, they have several disadvantages for the imaging darkfield system. One problem with a physical blockage type filter for the imaging darkfield system is that the optical response of the physical mask contains significant numbers of side lobes which can extend to 100 um, also referred herein as a "long range ringing response." There are two major problems with this long range ringing response. First, in today's semiconductor devices, the array or periodic structure regions are usually surrounded by bus regions, which appear bright during dark field inspection. The light in the bus regions leak into the array region, reducing the array region defect sensitivity. Second, the long-ranged ringing response couples the noise in the bus regions with the noise in the array regions. This is highly undesirable because this kind of noise coupling cannot be well characterized, adding uncertainty to the performance of the system.

In light of the foregoing, improved mechanisms for darkfield inspection are needed. It would be especially beneficial to have an imaging darkfield inspection system that substantially reduces or eliminates the long range ringing response produced by periodic or array structures on a specimen.

SUMMARY OF THE INVENTION

Accordingly, the present invention provides methods and apparatus for performing a darkfield inspection on a specimen having periodic structures thereon while substantially reducing or eliminating the long range ringing response that was typically produced by the traditional Fourier filter masks used to remove the signature caused by the periodic structures.

In one embodiment, an apparatus for inspecting a specimen by detecting optical beams scattered from the specimen. The apparatus includes a beam generator for providing and directing an incident beam towards a specimen and an array subtraction device for substantially subtracting a periodic component from an output beam scattered from the specimen in response to the incident beam. The periodic component corresponds to at least one periodic structure on the specimen, and the subtraction is performed so as to substantially reduce or eliminate a ringing response from the output beam. The subtraction is also performed so as to substantially prevent subtracting any actual defect components from the output beam. The apparatus further includes a detector for receiving the output beam and generating an output image or signal based on the output beam. In a further aspect, the apparatus also includes a controller for analyzing the output image or signal to determine whether there are any defects present on the specimen.

In a specific implementation, the array subtraction device is formed from a splitter for receiving the output beam before it reaches the detector and splitting the output beam into a first and a second secondary beam which are output from the splitter and a phase and pitch adjuster for receiving the first secondary beam, wherein the phase and pitch adjuster is configured to spatially shift the first secondary beam relative to the second secondary beam by an integer amount of a period of the periodic structure and reverse the polarity of the first or second secondary beam. In this implementation, the array subtraction device further includes a combiner for receiving the first secondary beam after it passes through the phase and pitch adjuster and for receiving the second secondary beam. The combiner is configured to combine the first and second secondary beams so that the periodic component is substantially subtracted from the combined output beam so as to substantially reduce or eliminate a ringing response and to substantially prevent subtracting any actual defect components from the combined output beam.

In a further aspect, the phase and pitch adjuster is formed from a rotatable mirror for receiving the first secondary beam, whose mirror position is selectable to achieve a specific spatial shift to correspond to an integer of the period of the periodic structure and a phase adjuster for receiving the first secondary beam and being configured to reverse the polarity of the first secondary beam. In a particular embodiment, the phase adjuster is in the form of a single wedge shaped element or two wedge shaped elements where it has an angled side of each wedge shaped element that is facing the other angled side of the other wedge shaped element. In this aspect, the phase adjuster is movable along a direction perpendicular to a path of the first secondary beam so as to achieve an odd integer of 180 degrees difference between the first and second secondary beams. In one aspect, the rotatable mirror is placed to receive the first secondary beam and reflect it towards the phase adjuster.

In yet another implementation, the array subtraction device also includes a path compensator for substantially matching the path of one of the secondary beams to the path of the other secondary beam. In another embodiment, the phase and pitch adjuster is in the form of an integrated unit that is movable along a direction perpendicular to a path of the first secondary beam. In this embodiment, the unit includes a de-centered spherical element for receiving the first secondary beam and spatially shifting the first secondary beam relative to the second secondary beam by an integer amount of a period of the periodic structure and a wedge shaped element for receiving the first secondary beam and adjusting a phase of the first secondary beam 180 degrees from a phase of the second secondary beam.

In a further aspect, the wedge shaped element is movable in the direction perpendicular to the path of the first secondary beam. The integrated unit and wedge shaped element are movable to achieve (1) spatially shifting the first secondary beam relative to the second secondary beam by an integer amount of a period of the periodic structure and (2) adjusting a phase of the first secondary beam 180 degrees from a phase of the second secondary beam.

In another implementation, the array subtraction device includes a plurality of splitters for receiving the output beam before it reaches the detector and splitting the output beam into n secondary beams. The array subtraction device also includes a plurality of pitch adjusters for receiving at least some of the n secondary beams from the splitters. The pitch adjusters are configured to perform a spatial pitch shift on each received secondary beam such that the periodic components of the secondary beams are shifted in position relative to each other by 1/n of a period of the periodic structure. The array subtraction device further includes a combiner to receive and combine the n secondary beams. The variable n is selected so that diffraction peaks of the combined output beam are outside a collection pupil of the apparatus and not received by the detector.

In another embodiment, the array subtraction device is formed from a spatial light modulator (SLM) positioned in the Fourier plane of the output beam and configured to substantially block the periodic component from the output beam while substantially reducing or eliminating the ringing response. In a further aspect, the SLM is configured with an amplitude profile that has a sinusoidal shape, where the profile is zero or crosses zero at the center of each diffraction peak produced by the periodic component. In another aspect, the SLM is configured so as to substantially block each diffraction peak of the periodic component and to partially and gradually block the remaining edge portions of each peak. In yet another aspect, the SLM is configured with varying transmission levels in positions that correspond to diffraction peaks of the periodic component so as to smoothly reduce an amplitude at the edges of the peaks. The array subtraction device may further include an aperture positioned at the Fourier plane to completely block areas outside a boundary of the diffraction pattern outer edge of the periodic component so as to minimize ringing at such edge.

In another embodiment, the array subtraction device includes a pre-fabricated sinusoidal mask positioned at the Fourier plane and a zoom lens positioned before the pre-fabricated sinusoidal mask. The magnification of the zoom lens is adjustable so that the period of the pre-fabricated sinusoidal mask substantially coincides with the period of the diffraction peaks produced by the periodic components. In a further aspect, the apparatus includes a second zoom lens to compensate for a change in pixel resolution caused by the first zoom lens.

Another aspect of the invention includes methods of, in addition to inspecting a specimen using any of the previously described apparatus embodiments.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Figure 1:
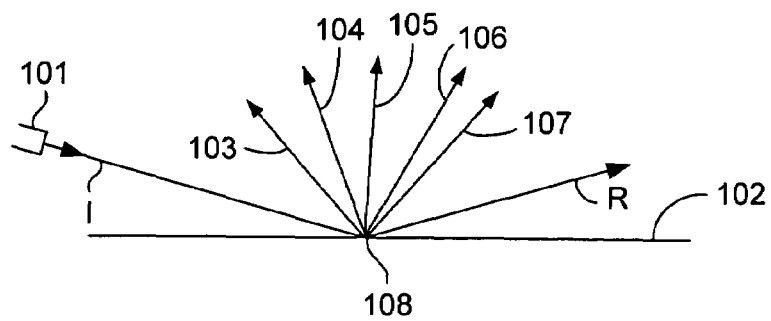
FIG. 1 illustrates aspects of light scattering used in dark-field inspection tools.

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, the present invention includes array suppression mechanisms that are arranged in the output path of an optical beam as it is directed from a specimen. The array suppression mechanism substantially reduces or eliminates portions of the output beam that are contributed by array or periodic structures on the specimen.

The novel array suppression device embodiments of the present invention are incorporated into an optical inspection system for inspecting samples with one or more incident optical beams. In general, such a system also provides a detector for detecting beams emanated from the specimen in response to the incident beam(s) provided by an illumination apparatus and directed towards the specimen.

In the exemplary inspection systems described herein, each incident beam may be in any suitable form of coherent light. For instance, more than one laser having different wavelengths including deep ultra violet, ultra violet, or visible light wavelengths can be used. Different wavelengths can be used to optimize for detecting defects with different characteristics, and a combination of several wavelengths can be advantageous for further reducing laser coherence and averaging out the effect of wafer film thickness variations. A dark field inspection is preferably performed with a very bright light source so as to detect small defects on a specimen by analyzing only the scattered light.

Additionally, any suitable lens arrangement may be used to direct the incident beams towards the specimen and direct the output beams emanating from the specimen towards a detector. The output beams may be scattered from the specimen surface or transmitted through the specimen. Likewise, any suitable type and number of detection elements may be used to receive the one or more output beams and provide an image or a signal based on the characteristics (e.g., intensity) of the received output beam(s).

The inspection system of the present invention are especially suitable for inspecting semiconductor devices or wafers, as well as reticles or masks. Other types of specimens which may be inspected or imaged using the inspection systems of the present invention include any surface, such as a flat panel display.

Figure 2:
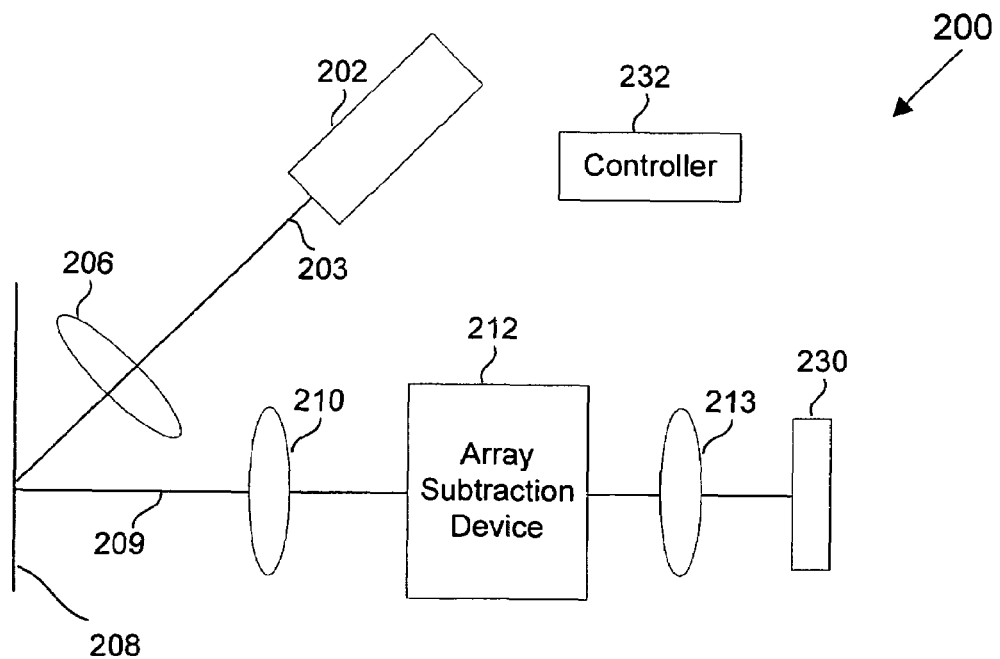
FIG. 2 is a diagrammatic representation of an optical inspection system in accordance with one embodiment of the present invention.

FIG. 2 is a diagrammatic representation of an optical inspection system 200 in accordance with one embodiment of the present invention. As shown, the inspection system 200 includes an optical beam generator 202 for producing and directing an incident beam 203 towards the specimen 208. The inspection system 200 also includes at least one or more lenses 206 for directing and focusing (if needed) the incident beam 203 onto the specimen 208.

In an alternative embodiment, the illumination source may be in the form of multiple illuminations sources which are selectively directed onto a plurality of optical fibers. These fibers then are arranged to output a plurality of incident beams with a spatial profile that is dependent on the selected illumination sources. The fibers may also be coupled with a fiber modulator which operates to substantially eliminate the speckle noise which may be present in the incident beams to thereby produce a more uniform, incoherent illumination. For example, the fiber modulator may be a piezoelectric modulator which operates to stretch the fibers so as to change the phase difference between the modes inside the multi-mode fibers to therefore reduce the spatial coherence to produce a speckle free illumination. Several embodiments of such an arrangement are further described in U.S. Provisional Application No. 60/533,741, entitled ILLUMINATION APPARATUS AND METHODS, filed 29 Dec. 2003, by Mehdi Vaez-Iravani and Guoheng Zhao, which application is incorporated herein by reference in its entirety.

Referring back to FIG. 2, the incident beam generally passes through a number of lenses which serve to relay the beam towards a specimen. For example, the incident beam passes through a lens (not shown) which collimates the incident beam and then through a lens (not shown) which converges the incident beam. The incident beam may then pass through objective lens (e.g., 206) which focuses the incident beam onto specimen 208 at one or more incident angles.

After the incident beam impinges on the specimen, the light is then reflected (and/or transmitted) and scattered from the specimen 208, which is referred to herein as "output light" or "output beam" 209. The inspection system may also include any suitable lens arrangements for directing the output light towards a detector. In the illustrated embodiment, the output light pass through objective lens 210, array subtraction device 212, and imaging optics 213 to detector 230.

The imaging lens 213 is generally used to form an image of the sample on the detector 230. A Fourier plane relay lens (not shown) may also be used to relay the Fourier plane of the specimen 208 to the array subtraction device 212. The array subtraction device 212 generally is operable to substantially reduce or eliminate components of the output beam which are caused by periodic or array structures on the specimen. The detector 230 may take any suitable form for detecting one or more optical output beams and generating either signals or an image from the output beam(s). By way of example, the detector may be in the form of a CCD (charge coupled device) or TDI (time delay integration) detector.

The inspection system 200 also may include a controller 232. The controller 232 may be any suitable combination of software and hardware and is generally configured to control various components of the inspection system 200. For instance, the controller may control selective activation of the illumination source 202, the illumination polarization state settings, array subtraction device settings, etc. The controller 232 may also receive the image or signal generated by the detector 230 and be configured to analyze the resulting image or signal to determine whether defects are present on the specimen, characterize defects present on the specimen, or otherwise characterize the specimen.

Figure 3:
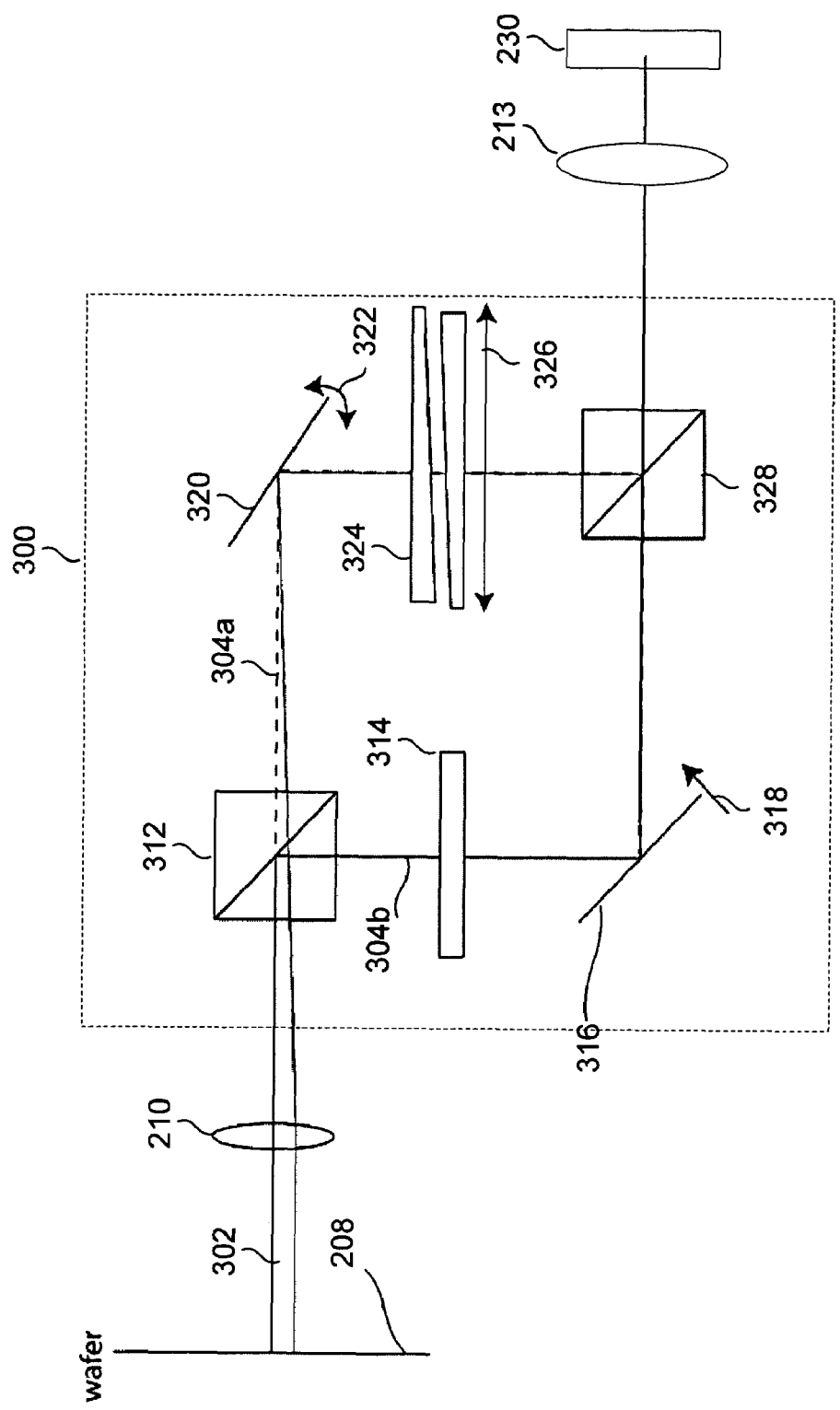
FIG. 3 is a diagrammatic representation of an array subtraction device in accordance with a specific implementation of the present invention.

FIG. 3 is a diagrammatic representation of an array subtraction device 300 in accordance with a specific implementation of the present invention. Only the output path of the inspection system is shown in this illustration. A scattered output beam 302 leaves the specimen 208 and passes through lens 210 to array subtraction device 300. The array subtraction device 300 generally acts to filter the array or periodic components from the output beam 302 before the output beam 302 passes through imaging optics 213 and impinges on the detector 230 so that ringing is substantially reduced or eliminated without eliminating the defect components from the output beam.

In general the array subtraction device of this and some of the other embodiments of the present invention split the output beam into two or more secondary output beams. At least one of the secondary output beams is then manipulated so that when it is recombined with the other one or more secondary output beam(s), the periodic structure components are substantially subtracted from the combined output beam before it reaches the detector 230 while a ringing response is substantially eliminated and any defect components are not substantially subtracted from the combined output beam. After at least one of the two secondary beams 304a and 304b are manipulated by array subtraction device 300, they both are then combined as beam 304b passes through splitter 328 and beam 304a is reflected off splitter 328. The combined beam then impinges on detector 230.

Figure 4A:
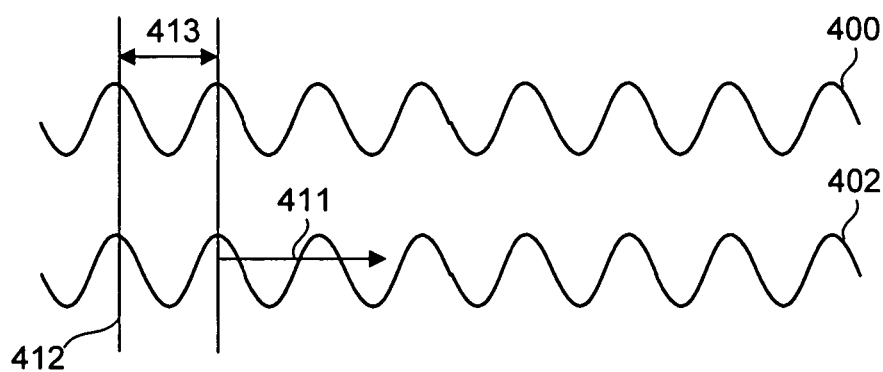
FIGS. 4A through 4C are graphs illustrating the effects of an array subtraction device on a typical output beam in accordance with one embodiment of the present invention.
Figure 4B:
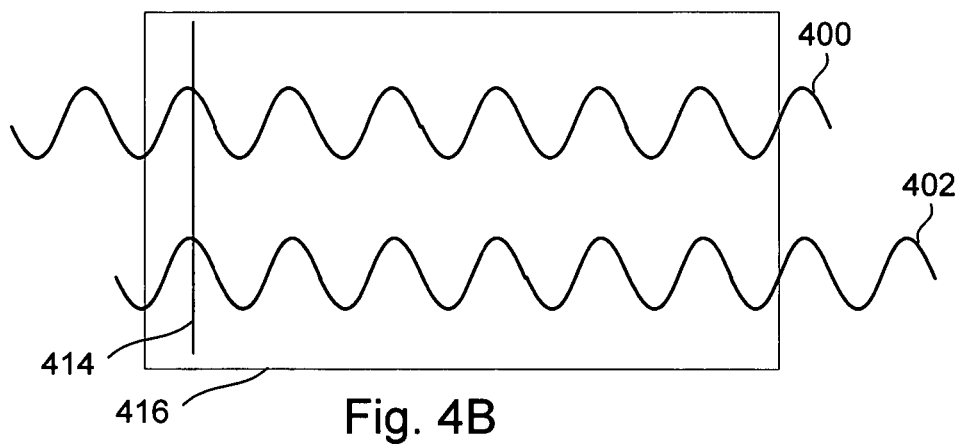
Figure 4C:
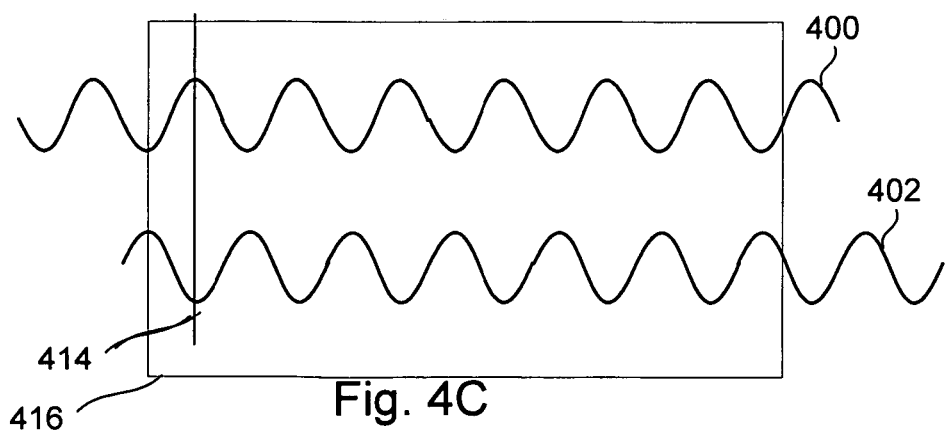

FIGS. 4A through 4C are graphs illustrating the effects of an array subtraction device on a typical output beam in accordance with one implementation of the present invention. In this example, the output beam has periodic structure components which result in a sinusoidal-shaped output beam. The goal of the array subtraction device is to substantially subtract this sinusoidal component and not the defect components from the output beam.

One way to substantially subtract the sinusoidal component resulting from a periodic structure on the specimen is to spatially shift one of the secondary output beams relative to the other by a period of the periodic structure and reverse its polarity before combining the two secondary output beams. FIG. 4A shows the two different secondary output beams 400 and 402 which are the result of an output beam being split into two different secondary beams. One of the secondary output beams may be shifted spatially by a period of the array structure so that the defect components are not eliminated along with the periodic structure components. For example, secondary beam 402 is shifted in direction 411 by amount 413 relative to secondary beam 400. FIG. 4B show the result of shifting secondary output beam 402 by a period of the structure without reversing the polarity of the secondary beam. Preferably, this shifting results in the structures remaining in the collection field of view, e.g., 416 of FIGS. 4B and 4C. As a result, the secondary beams 400 and 402 still have a same alignment, e.g., 414, as shown in FIG. 4B. One of the secondary beams' polarity is then reversed with respect to the other secondary beam. FIG. 4C illustrates the reversal of the polarity of the secondary output beam 402.

When the two secondary output beams are combined, the sinusoidal or periodic structure component of the original output beam is substantially subtracted from the combined output beam without eliminating the actual defects. This subtraction is possible since one of the secondary beams has been shifted spatially relative to another secondary beam by an integer amount of an array cell size and an odd integer amount of $\pi$ for the phase so as to achieve a reverse polarity between the secondary beams.

Alternatively, the output beam may be split into n beams or paths. The pitch adjusters of the beam are then tuned such that the periodic pattern from each path is shifted in position by 1/n of the array period relative to each other. The n output beams from each path are then recombined to form a new array pattern with period of $1/n^{th}$ of the optical period. The variable n may be selected so that the locations of the all the diffraction peaks are outside the collection pupil, thereby, removing the periodic structure from the detected signal.

Referring back to the illustrated implementation of FIGS. 4A-4D, shifting the period position and phase of a one of the secondary beams may be accomplished in any suitable manner and by any suitable combination of hardware and/or software. In the embodiment of FIG. 3, the array subtraction device 300 includes a splitter 312 for splitting the output beam 302 into a first secondary beam 304a and a second secondary beam 304b. The first beam 304a is reflected off a pitch adjuster 320 which is rotatable in direction 322. The first beam 304a then passes through phase adjuster 324 which is movable along a direction 326 that is perpendicular to the optical path of first beam 304a.

In general, the pitch adjuster 320 spatially shifts the signal of the secondary output beam 304a relative to the secondary beam 304b, while the phase adjuster 324 reverses the polarity or sign of the electric field of the secondary beam 304a. For example as illustrated in FIG. 4A, the pitch adjuster 320 would shift beam 400 in direction 410 relative to beam 402, and the phase adjuster 324 results in a reverse polarity for one of the beams, e.g., beam 400. These two devices may be interchangeably placed so as to adjust the pitch and phase in any suitable order.

In sum, the pitch and phase adjuster are configured to spatially shift one of the secondary beams relative to another secondary beam by an integer amount of the structure period and phase shift one of secondary beams relative to the other beam an odd integer amount of $\pi$ so as to achieve a reverse polarity between the secondary beams. One secondary beam is spatially shifted relative to the other beam by a period of the structure because when one of the secondary beams is reversed in polarity and then combined with the other secondary beam, the defects are not subtracted from the combined beam but only the periodic structures. That is, if a phase shift of 180 degrees was merely performed on one of the secondary beams without performing a spatial shift, the defect components would also be subtracted from the combined output beam.

The pitch adjuster 320 and phase adjuster 324 may be constructed in any suitable manner to perform the above described operations, e.g., shifting pitch and reversing polarity. An integrated device for performing both pitch and phase shifting may also be used. In the illustrated embodiment, the pitch adjuster 320 is a rotatable mirror that can be automatically adjusted, e.g., via controller 232, to result in a particular shift for secondary beam 304a. That is, the mirror's rotational position corresponds to a particular spatial shift in secondary beam 304a. Thus, the pitch adjuster may be configured for different periodic structures which have different period lengths.

In one implementation, the phase adjuster 324 is in the form of a double wedge shaped element that is movable along a direction that is perpendicular to the secondary output beam path. This movement causes the secondary beam to exit the slope of a first wedge at a particular thickness point of the wedge which affects the amount of rotation of the phase of the secondary beam. In other implementations, the phase adjuster 324 is in the form of single wedge element. Moving the phase adjuster 324 relative to the secondary output beam allows a reverse polarity between the two secondary beams produced from any illumination angle. In general, the amount of phase shift needed to ensure a reverse polarity between the two secondary beams changes with array pitch and the incident angle of illumination. Since the period of the periodic components varies depending on the device, it is preferable to have component 324 be adjustable.

The array subtraction device 300 may also include a path compensator 314 for adjusting one of the optical output paths to substantially match the other output path. In the example of FIG. 3, a path compensator 314 is placed in the path of the secondary beam 304b. The path compensator may take any suitable form for adjusting the effective path length of an optical beam. In a specific implementation, the path compensator 314 is in the form of a corrector plate having a particular thickness and material composition for matching the path of beam 304b with the path of beam 304a. The exact specifications of the path compensator 314 may be determined after the specific path lengths of each secondary beam path is measured or determined. The path compensator may then be designed to compensate for the discrepancy between the two secondary paths.

A reflective mirror 316 may also be provided to direct the secondary beam 304b towards the splitter 328. This mirror 316 may also be movable so as to provide the coaxial alignment between the two secondary beams.

In an alternative implementation, the array subtraction device does not include a path compensator, and the optical components in the secondary output beam paths may be then carefully matched to result in substantially same path lengths. In yet an alternative implementation, the array subtraction device does not include a path compensator and the optics in each secondary path are not designed to result in a substantially same path. In this later case, the pitch adjuster is configured to adjust for the difference between the paths so that the periods of each secondary beam are aligned.

Figure 5:
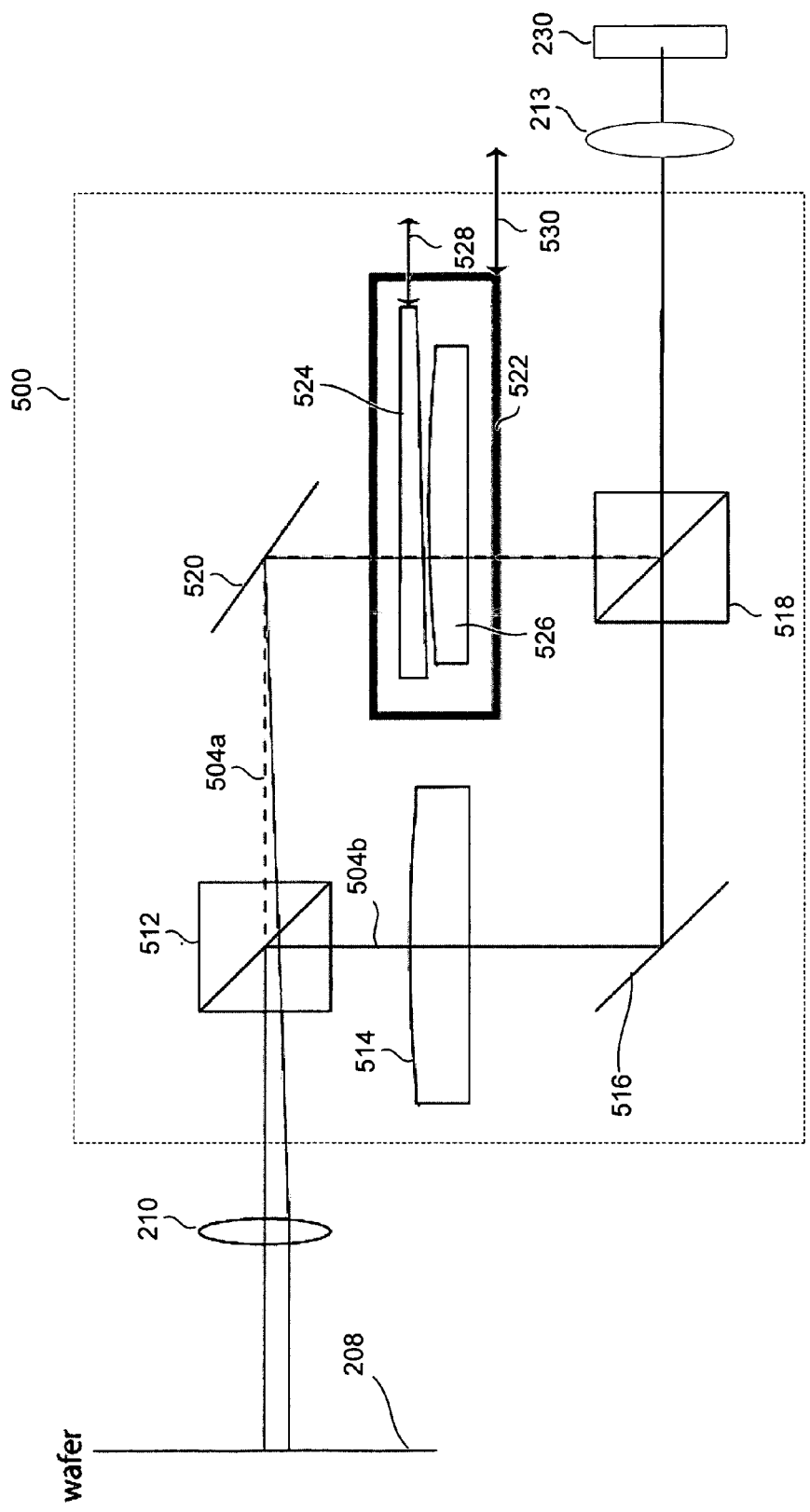
FIG. 5 is a diagrammatic representation of an array subtraction device in accordance with another implementation of the present invention.

FIG. 5 is a diagrammatic representation of an array subtraction device 500 in accordance with another implementation of the present invention. This embodiment is similar to the embodiment of FIG. 3, except there is no separate rotating pitch adjuster. As shown in FIG. 5, the position of mirror 520 is fixed. Instead, the array subtraction device 500 includes an integrated phase and pitch adjuster unit 522 within the path of secondary beam 504a. This unit 522 contains a pitch adjuster 526 and a phase adjuster 524. The unit 522 is preferably movable in direction 530, while the phase adjuster 524 is independently movable relative to the pitch adjuster 526. Alternatively, the pitch adjuster 526 is movable relative to the phase adjuster 524. However, this arrangement may be more difficult to ascertain the correct position for achieving the goals of the array subtraction device since moving the pitch adjuster element would tend to change both the pitch and phase. This array subtraction device 500 may also optionally include a path compensator 514 within the path of secondary beam 504b, similar to the device 400 of FIG. 4.

The pitch adjuster may take any suitable form for spatially shifting the secondary beam. In one implementation, the pitch adjuster 526 is a de-centered spherical element. In other implementations, the pitch adjuster 526 is in the form of a spherical lens, a planar convex lens, etc. Likewise, the phase adjuster may take any suitable form for adjusting the phase of the secondary beam. In one implementation, the phase adjuster 524 is in the form of a wedge shaped element to apply a tilting or rotating operation on the secondary beam 504a as it passes through the angled edge of this element.

Figure 6B:
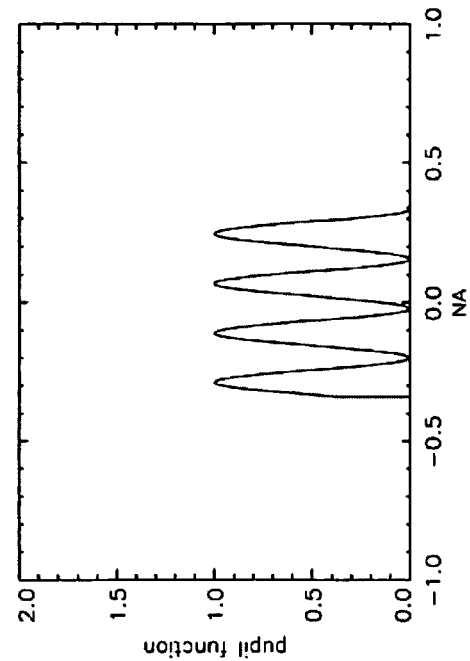
FIG. 6B is a graph illustrating the pupil function of the SLM of FIG. 6A in accordance with another embodiment of the present invention.
Figure 6A:
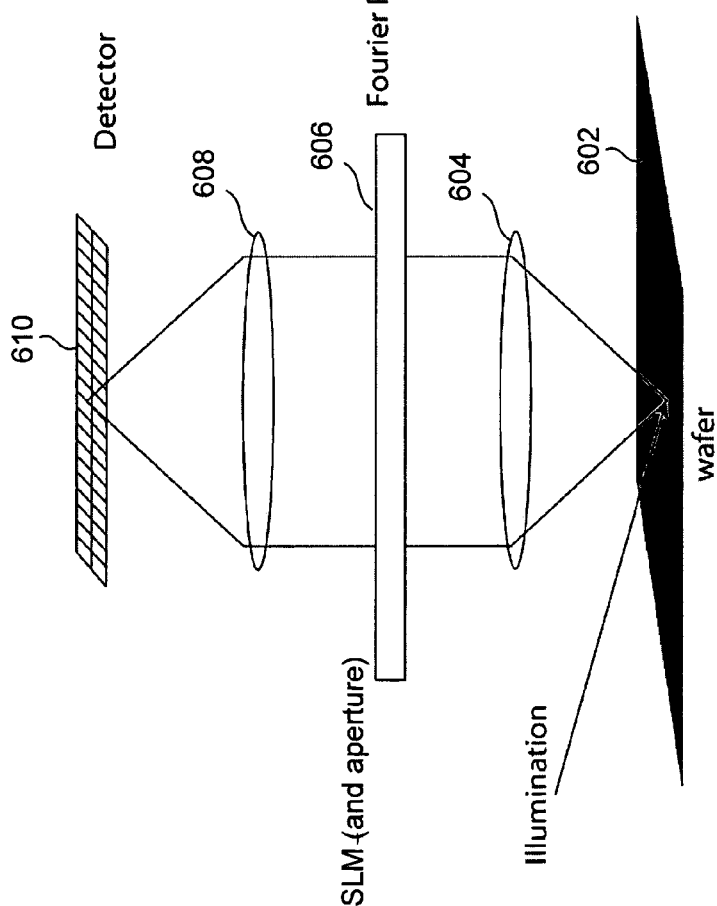
FIG. 6A is a diagrammatic representation of an array subtraction device in the form of a spatial light modulator (SLM) in accordance with yet another implementation of the present invention.

FIG. 6A is a diagrammatic representation of an array subtraction device in the form of a spatial light modulator (SLM) in accordance with another implementation of the present invention. In this embodiment, the transmission profile of the SLM follows a sinusoidal profile which is generated by using a finite sum of sinusoidal functions of different frequencies, where the number of frequencies is substantially limited, for example no more than 10, to substantially remove the periodic components and mostly importantly to avoid ringing. Of course, any suitable combination of cosine and/or sine functions may be used to achieve the desired effects as described further below. As used by those skilled in the art, the term "sinusoidal" is used herein to include any suitable combination of cosine and/or sine functions. As shown in FIG. 6A, an illumination beam (the illumination source and optics are not shown) is directed towards the specimen 602. An output beam is then scattered from the specimen 602 towards detector 610. Optics 604 and 608 are configured to direct and focus the beam towards detector 610.

SLM 606 is placed within the Fourier plane of the output beam. The pupil profile SLM is configured to be sinusoidal so that the resultant effect is to substantially block the contribution of the array or periodic (non-defective) structures from the output beam while substantially reducing or eliminating ringing. FIG. 6B illustrates a pupil profile of the SLM 606 for the periodic components of an example output beam. Said in another way, with the sinusoidal pupil function, the diffraction peaks of the periodic components are blocked without an abrupt cutoff; hence, no long range ringing response is created. Of course, any suitable blocking function, besides sinusoidal, may be used that results in a gradual or smooth blocking function at the edge areas of the periodic structure components so as to substantially reduce ringing.

Any suitable SLM may be used that is configurable with varying transmission levels. For example, a liquid crystal based SLM manufactured by Meadowlark Optics of Frederick, Colo. is suitable. In an optional implementation, the SLM 506 includes a hard aperture that is configured to substantially close at the boundary of the diffraction patterns outer edge so as to minimize ringing at the edges of the field of view.

Figure 7:
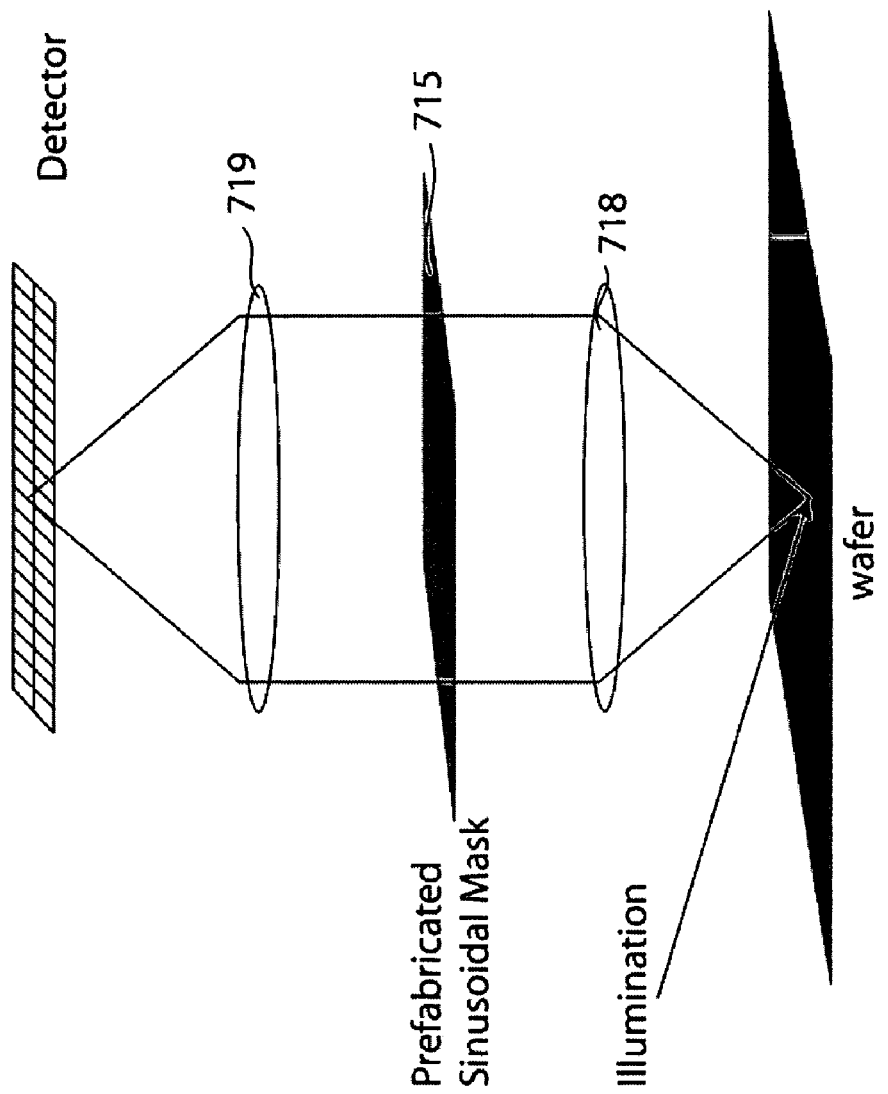
FIG. 7 is a diagrammatic representation of an array subtraction device in accordance with another alternative implementation of the present invention.

FIG. 7 is a diagrammatic representation of an array subtraction device in accordance with another alternative implementation of the present invention. Instead of an SLM, a set of one or more fixed (e.g., pre-fabricated) sinusoidal masks 715 is positionable in the Fourier plane of the system. A zoom lens 718 in front of the fixed (e.g., pre-fabricated) sinusoidal one or more masks 715 is used so that the period of the diffraction peaks produced by the periodic components is magnified or de-magnified to coincide with the period of a selected one or more sinusoidal masks. In the illustrated embodiment, a one or more sinusoidal mask may be selectively positioned at the Fourier plane for a particular zoom setting. For example, a first mask may be suitable for a first zoom range, while a second mask is suitable for a second zoom range. The amount of magnification of the zoom lens is adjustable so that the diffraction peaks and the minimum of the sinusoidal profile are substantially aligned. A second zoom lens 719 behind the pre-fabricated mask may be needed so that the pixel size of the image is preserved.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. An apparatus for inspecting a specimen by detecting optical beams scattered from the specimen, comprising:
    a beam generator for providing and directing an incident beam towards a specimen;
    an array subtraction device arranged to split an output beam, scattered from the specimen in response to the incident beam, into at least two secondary beams, spatially shift the at least two secondary beams relative to each other, and then recombine the secondary beams, wherein the recombining of the secondary beams causes (i) a periodic component, corresponding to at least one periodic structure on the specimen, to be subtracted from the recombined output beam, (ii) a ringing response to be substantially reduced or eliminated from the recombined output beam, and (iii) any actual defect components to be prevented from being subtracted from the recombined output beam; and
    a detector for receiving the recombined output beam and generating an output image or signal based on the recombined output beam.

2. An apparatus as recited in claim 1, further comprising a controller for analyzing the output image or signal to determine whether there are any defects present on the specimen.

3. An apparatus as recited in claim 1, wherein the array subtraction device comprises:
    a splitter for receiving the output beam before it reaches the detector and splitting the output beam into a first and a second secondary beam which are output from the splitter;
    a phase and pitch adjuster for receiving the first secondary beam, wherein the phase and pitch adjuster is configured to spatially shift the first secondary beam relative to the second secondary beam by an integer amount of a period of the periodic structure and reverse the polarity of the first or second secondary beam; and
    a combiner for receiving the first secondary beam after it passes through the phase and pitch adjuster and for receiving the second secondary beam, wherein the combiner is configured to combine the first and second secondary beams so that the periodic component is substantially subtracted from the combined output beam so as to substantially reduce or eliminate a ringing response and to substantially prevent subtracting any actual defect components from the recombined output beam.

4. An apparatus as recited in claim 1, wherein the array subtraction device further comprises a plurality of splitters arranged to receive the output beam before it reaches the detector and split the output beam into n secondary beams perform a spatial pitch shift the n secondary beams relative to each other such that the periodic components of the secondary beams are shifted in position relative to each other by 1/n of a period of the periodic structure, and a plurality of pitch adjusters that are configured to receive and combine the n secondary beams after they are shifted relative to one another, wherein n is selected so that diffraction peaks of the combined output beam are outside a collection pupil of the apparatus and not received by the detector.

5. An apparatus as recited in claim 3, wherein the phase and pitch adjuster comprises:
    a rotatable mirror for receiving the first secondary beam, whose mirror position is selectable to achieve a specific spatial shift to correspond to an integer of the period of the periodic structure; and
    a phase adjuster for receiving the first secondary beam and being configured to reverse the polarity of the first secondary beam.

6. An apparatus as recited in claim 5, wherein the phase adjuster is in the form of a single wedge shaped element or two wedge shaped elements, which have an angled side of each wedge shaped element that is facing the other angled side of the other wedge shaped element, and wherein the phase adjuster is movable along a direction perpendicular to a path of the first secondary beam so as to achieve an odd integer of 180 degrees difference between the first and second secondary beams.

7. An apparatus as recited in claim 5, wherein the rotatable mirror is placed to receive the first secondary beam and reflect it towards the phase adjuster.

8. An apparatus as recited in claim 3, wherein the array subtraction device further comprises a path compensator for substantially matching the path of one of the secondary beams to the path of the other secondary beam.

9. An apparatus as recited in claim 3, wherein the phase and pitch adjuster is in the form of an integrated unit that is movable along a direction perpendicular to a path of the first secondary beam, wherein the integrated unit comprises:
    a de-centered spherical element for receiving the first secondary beam and spatially shifting the first secondary beam relative to the second secondary beam by an integer amount of a period of the periodic structure; and
    a wedge shaped element for receiving the first secondary beam and adjusting a phase of the first secondary beam 180 degrees from a phase of the second secondary beam.

10. An apparatus as recited in claim 9, wherein the wedge shaped element is movable in the direction perpendicular to the path of the first secondary beam, wherein the integrated unit and wedge shaped element are movable to achieve (1) spatially shifting the first secondary beam relative to the second secondary beam by an integer amount of a period of the periodic structure and (2) adjusting a phase of the first secondary beam 180 degrees from a phase of the second secondary beam.

11. An apparatus for inspecting a specimen by detecting optical beams scattered from the specimen, comprising:
    a beam generator for providing and directing an incident beam towards a specimen;
    an array subtraction device for substantially subtracting a periodic component from an output beam scattered from the specimen in response to the incident beam, wherein the periodic component corresponds to at least one periodic structure on the specimen, wherein the array subtraction device comprises a spatial light modulator (SLM) or pre-fabricated sinusoidal mask positioned in the Fourier plane of the output beam and configured or arranged to receive the output beam and substantially block transmission of each diffraction peak of the periodic component from the received output beam and to partially and gradually block transmission of the remaining edge portions of each peak from the received output beam so as to cause a gradual decrease in transmission at the remaining edge portions while substantially reducing or eliminating the ringing response; and
    a detector for receiving the output beam after it is partially transmitted through the SLM and generating an output image or signal based on the output beam after it is partially transmitted through the SLM.

12. An apparatus as recited in claim 11, wherein the array subtraction device comprises an SLM and the SLM is configured with an amplitude profile that substantially coincides with the centers of the diffraction peaks of the periodic component.

13. An apparatus as recited in claim 11, wherein the array subtraction device comprises an SLM and the SLM is configured with varying transmission levels in positions that correspond to peaks of the periodic component so as to smoothly reduce an amplitude at the edges of the peaks.

14. An apparatus as recited in claim 13, the array subtraction device further comprising an aperture positioned at the Fourier plane to completely block areas outside a boundary of the diffraction pattern outer edge of the periodic component so as to minimize ringing at such edge.

15. An apparatus as recited in claim 11, wherein the array subtraction device comprises:
- a pre-fabricated sinusoidal mask positioned at the Fourier plane; and
- a zoom lens positioned before the pre-fabricated sinusoidal mask, wherein the magnification of the zoom lens is adjustable so that the period of the pre-fabricated sinusoidal mask substantially coincides with the period of the diffraction peaks produced by the periodic components.

16. An apparatus as recited in claim 15, further comprising a second zoom lens to compensate for a change in pixel resolution caused by the first zoom lens.

17. A method for inspecting a specimen, comprising:
- providing and directing an incident beam towards a specimen;
- splitting an output beam, scattered from the specimen in response to the incident beam, into at least two secondary beams
- spatially shifting the at least two secondary beams relative to each other; and
- recombining the secondary beams so as to substantially reduce or eliminate a ringing response from the recombined output beam, wherein the recombining of the secondary beams causes (i) a periodic component, corresponding to at least one periodic structure on the specimen, to be subtracted from the recombined output beam, (ii) a ringing response to be substantially reduced or eliminated from the recombined output beam, and (iii) any actual defect components to be prevented from being subtracted from the recombined output beam; and
- receiving the recombined output beam and generating an output image or signal based on the recombined output beam.

18. A method as recited in claim 17, wherein the subtraction operation is accomplished by:
- splitting the output beam into a first and a second secondary beam;
- spatially shifting the first secondary beam relative to the second secondary beam by an integer amount of a period of the periodic structure and reverse the polarity of the first or second secondary beam; and
- combining the first and second secondary beams so that the periodic component is substantially subtracted from the recombined output beam so as to substantially reduce or eliminate a ringing response and to substantially prevent subtracting any actual defect components from the recombined output beam.

19. A method for inspecting a specimen, comprising:
- providing and directing an incident beam towards a specimen;
- substantially subtracting a periodic component from an output beam scattered from the specimen in response to the incident beam, wherein the periodic component corresponds to at least one periodic structure on the specimen, wherein the subtraction operation is accomplished by receiving the output beam and substantially blocking transmission of each diffraction peak of the periodic component from the received output beam and partially and gradually blocking transmission of the remaining edge portions of each peak from the received output beam so as to cause a gradual decrease in transmission at the remaining edge portions while substantially reducing or eliminating the ringing response; and
- receiving the output beam and generating an output image or signal based on the output beam.

20. The method as recited in claim 19, wherein the subtraction operation further includes completely blocking areas outside a boundary of the diffraction pattern outer edge of the periodic component so as to minimize ringing at such edge.

* * * * *